(12) United States Patent
McLoone

(10) Patent No.: US 11,554,031 B2
(45) Date of Patent: Jan. 17, 2023

(54) ATTACHMENT PLATE FOR A PROSTHETIC SOCKET

(71) Applicant: Anclote Manufacturing Company, Inc., Largo, FL (US)

(72) Inventor: Kevin McLoone, Largo, FL (US)

(73) Assignee: ANCLOTE MANUFACTURING COMPANY, INC., Largo, FL (US)

( * ) Notice: Subject to any disclaimer, the term of this patent is extended or adjusted under 35 U.S.C. 154(b) by 96 days.

(21) Appl. No.: 17/030,949

(22) Filed: Sep. 24, 2020

(65) Prior Publication Data

US 2021/0000622 A1 Jan. 7, 2021

Related U.S. Application Data

(63) Continuation-in-part of application No. 16/803,437, filed on Feb. 27, 2020, now Pat. No. 11,109,987.

(60) Provisional application No. 62/905,006, filed on Sep. 24, 2019, provisional application No. 62/812,464, filed on Mar. 1, 2019.

(51) Int. Cl.
*A61F 2/80* (2006.01)
*A61F 2/50* (2006.01)

(52) U.S. Cl.
CPC ........ *A61F 2/80* (2013.01); *A61F 2002/5032* (2013.01); *A61F 2002/805* (2013.01)

(58) Field of Classification Search
CPC .................. A61F 2/80; A61F 2002/802; A61F 2002/805; A61F 2002/5032
See application file for complete search history.

(56) References Cited

U.S. PATENT DOCUMENTS

| | | | | |
|---|---|---|---|---|
| 6,063,125 | A * | 5/2000 | Arbogast | A61F 2/76 |
| | | | | 623/34 |
| 6,287,345 | B1 * | 9/2001 | Slemker | A61F 2/80 |
| | | | | 623/33 |
| 8,211,187 | B2 * | 7/2012 | Slemker | A61F 2/80 |
| | | | | 623/34 |
| 8,343,233 | B2 * | 1/2013 | Perkins | A61F 2/80 |
| | | | | 623/33 |
| 10,759,138 | B2 * | 9/2020 | Ruiz | B32B 27/065 |
| 2008/0086218 | A1 | 4/2008 | Eglisson | |
| 2008/0221705 | A1 | 11/2008 | Scussel | |
| 2010/0094432 | A1 * | 4/2010 | Mackenzie | A61F 2/68 |
| | | | | 623/34 |
| 2016/0058583 | A1 | 3/2016 | Hines | |
| 2018/0055661 | A1 | 3/2018 | Erdmann et al. | |
| 2019/0008663 | A1 | 1/2019 | Cheng et al. | |

* cited by examiner

*Primary Examiner* — Bruce E Snow
(74) *Attorney, Agent, or Firm* — Burr & Forman LLP; Jeffrey H. Kamenetsky

(57) ABSTRACT

The attachment plate for a prosthetic socket is fabricated into the distal end of a prosthetic socket. The attachment plate comprises a body with a peripheral seal, a valve, an air tunnel, and an exhaust port. When fastened in the distal end of a prosthetic socket, the peripheral seal creates a secure seal to the inner wall of the prosthetic socket and the exhaust port remains exposed to atmosphere. The valve is open to the cavity of the prosthetic socket for air to be removed to secure a prosthetic via vacuum or suction. Air from the cavity moves through the valve, through an air tunnel machined into the cylindrical body, and is expelled out of the exhaust port.

12 Claims, 6 Drawing Sheets

ATTACHMENT PLATE FOR A PROSTHETIC SOCKET

CROSS-REFERENCE TO RELATED APPLICATION

The application claims the benefit of U.S. Provisional Patent App. No. 62/905,006 titled Attachment Plate for a Prosthetic Socket, filed on Sep. 24, 2019, the disclosure of which is incorporated by reference. The application is a continuation-in-part of U.S. patent application Ser. No. 16/803,437 titled Vacuum Device for a Prosthetic filed on Feb. 27, 2020, which is a continuation-in-part of U.S. Provisional App. No. 62/812,464 titled Device for Creating an Elevated Vacuum in a Prosthetic filed on Mar. 12, 2019, the disclosures of which are incorporated by reference.

FIELD

The present disclosure relates to a prosthetic device for individuals that have had an amputation of one of their limbs and more particularly to an attachment plate and distal cushion that is configured to create suction in a prosthetic socket by expelling air, or utilized to pull elevated vacuum from an external source.

BACKGROUND

The most common cause of amputation is vascular related, although traumatic injuries and rare diseases may be a cause as well. In order to have a good functional prosthesis regardless of the cause of amputation, the prosthesis must have both good comfort and good suspension. If the suspension is not present, the leg will not stay on the user. If comfort is not maintained, the user cannot wear the prosthesis for extended periods of time Prosthetic limbs may be attached to the residual limb in various ways. Prosthetic limbs may be suspended from a user's body by a pulley, belt, or strap suspension. Prosthetic limbs may also be secured by a suspension sleeve that is rolled over the residual limb and the prosthetic socket. Other methods include mechanical or electric pumps to establish positive or negative pressures. However, many of these systems look unnatural, are heavy, and are often difficult to use or adjust. Furthermore, these systems may require pressures that are so forceful that they can be uncomfortable or cause damage to the residual limb tissue.

One issue with prosthetic suction sockets, or sockets for elevated vacuum, is leaks. There is a need for a need for a prosthetic socket with an attachment plate that can be used with standard suction sockets, or could have an external pump connected to the attachment plate for elevated vacuum.

SUMMARY

In one embodiment, the attachment plate is a metal cylindrical plate fabricated into the distal end of a prosthetic socket with a peripheral seal around the side of the cylindrical body to create an air-tight seal to the socket wall. The cylindrical body has a valve in the center with a removable filter above the seal.

A distal end pad may be affixed to a top of the cylindrical body. The distal end pad may have a channel running from a bottom of the distal end pad above the filter to the top of the distal end pad to the cavity of the prosthetic socket. The distal end pad may be formed to match the shape of a residual limb, and a port on the side to dump air and moisture on the side of the prosthesis eliminating corrosion on the inside of the structural pylon or pyramid which is not seen by visual inspection of follow up visits.

In another embodiment, the attachment plate to be fabricated into a prosthetic socket may comprise a cylindrical body, having a side, a top, and a bottom; a peripheral seal affixed to the side of the body; a valve affixed to the cylindrical body in fluid communication with a cavity of the prosthetic socket; and a port on the side of the body in fluid communication with the valve. The attachment plate may include an air tunnel through the body from the valve to the port. The exhaust port is configured to expel air external to a cavity of the prosthetic socket In one exemplary embodiment, the attachment plate comprises a distal end pad affixed to the top of the body; and a channel in the distal end pad fluidly connecting the cavity of the prosthetic socket to the valve.

In some embodiments, the distal end pad has a flat bottom and a concave top.

In some embodiments, the prosthetic socket is fabricated around the cylindrical body. In one exemplary embodiment, the cylindrical body forms a bottom end of the prosthetic socket with the peripheral seal secured against an inner surface of the prosthetic socket.

In one embodiment of the attachment plate, the cylindrical body includes a mounting element located on the bottom of the cylindrical body to connect or attach an artificial limb.

In another embodiment, the attachment plate may be fabricated into a distal end of a prosthetic socket. The attachment plate may include a cylindrical body having a top, a bottom, and a side; an exhaust port on the side of the cylindrical body; a peripheral seal affixed to the side of the cylindrical body and above the exhaust port, the peripheral seal contacting an inner surface of the distal end of the prosthetic socket to form an air-tight seal; a valve in the top of the cylindrical body, the valve in fluid communication with a cavity of the prosthetic socket; and an air tunnel running through the cylindrical body and connecting the valve to the exhaust port.

In another embodiment, the attachment plate may include a distal end pad positioned on the top of the cylindrical body and extending into the cavity of the prosthetic socket.

In one embodiment, the distal end pad includes a channel that allows air to move from the cavity to the valve to be expelled out of the exhaust port.

In one embodiment, a removable filter may be affixed over the valve to prevent debris from the cavity to enter the valve or the air tunnel.

Another embodiment of the attachment plate fabricated into a distal end of a prosthetic socket may comprise a cylindrical body having a peripheral seal, the peripheral seal configured to create an air-tight seal when the attachment plate is fabricated into the distal end of the prosthetic socket; a valve affixed on a top of the cylindrical body, the valve configured to allow air to flow out of a cavity of the prosthetic socket; an exhaust port in fluid communication with the valve, the exhaust port configured to expel air to atmosphere; and a mounting element, the mounting element configured to attach to a prosthetic limb.

In some embodiments, the attachment plate includes an air tunnel running through the cylindrical body from the valve to the exhaust port fluidly connecting the cavity to the exhaust port.

In some embodiments, the exhaust port is configured to attach to a mechanical or electric vacuum pump.

In another embodiment, the attachment plate includes a distal end pad having a channel; the distal end pad affixed on a top of the cylindrical body; the channel through the distal end pad configured to allow air to pass from the cavity to the valve.

DETAILED DESCRIPTION

Figure 1:
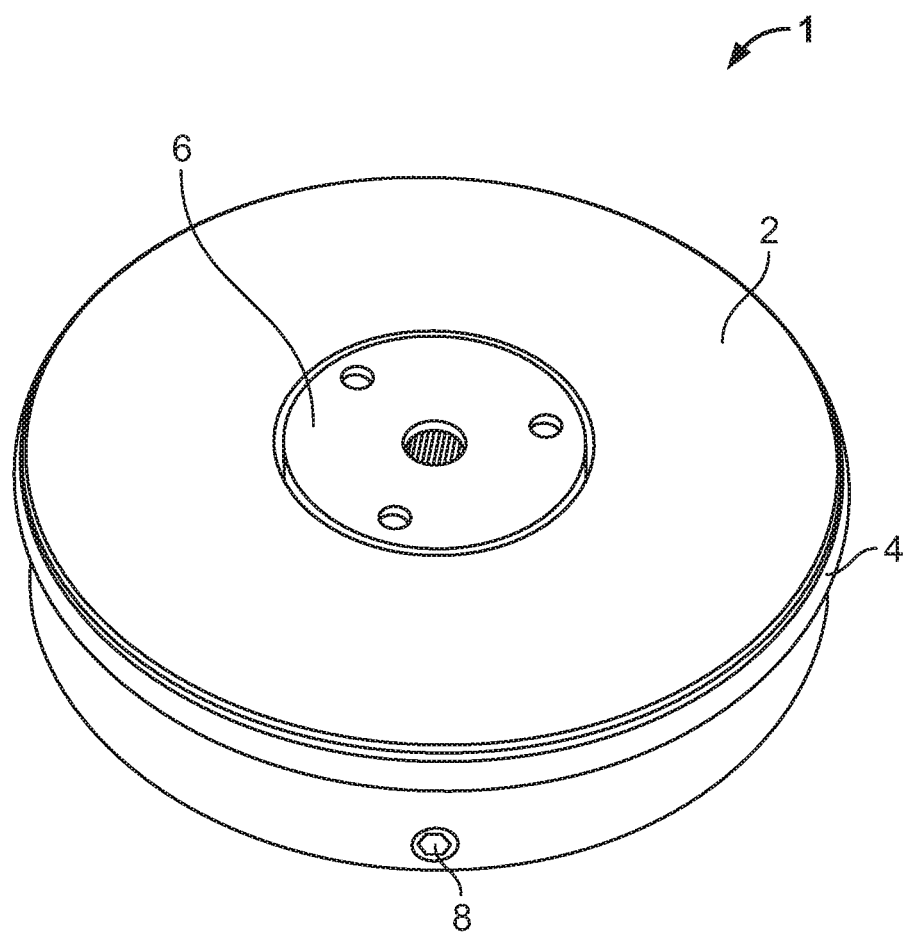
FIG. 1 illustrates an exemplary embodiment of the attachment plate for a prosthetic socket.

Reference will now be made in detail to the following exemplary embodiments, which are illustrated in the accompanying drawings, wherein like reference numerals refer to like elements throughout. The exemplary embodiments may be embodied in various forms without being limited to the exemplary embodiments set forth herein. Descriptions of well-known parts are omitted for clarity.

Figure 2:
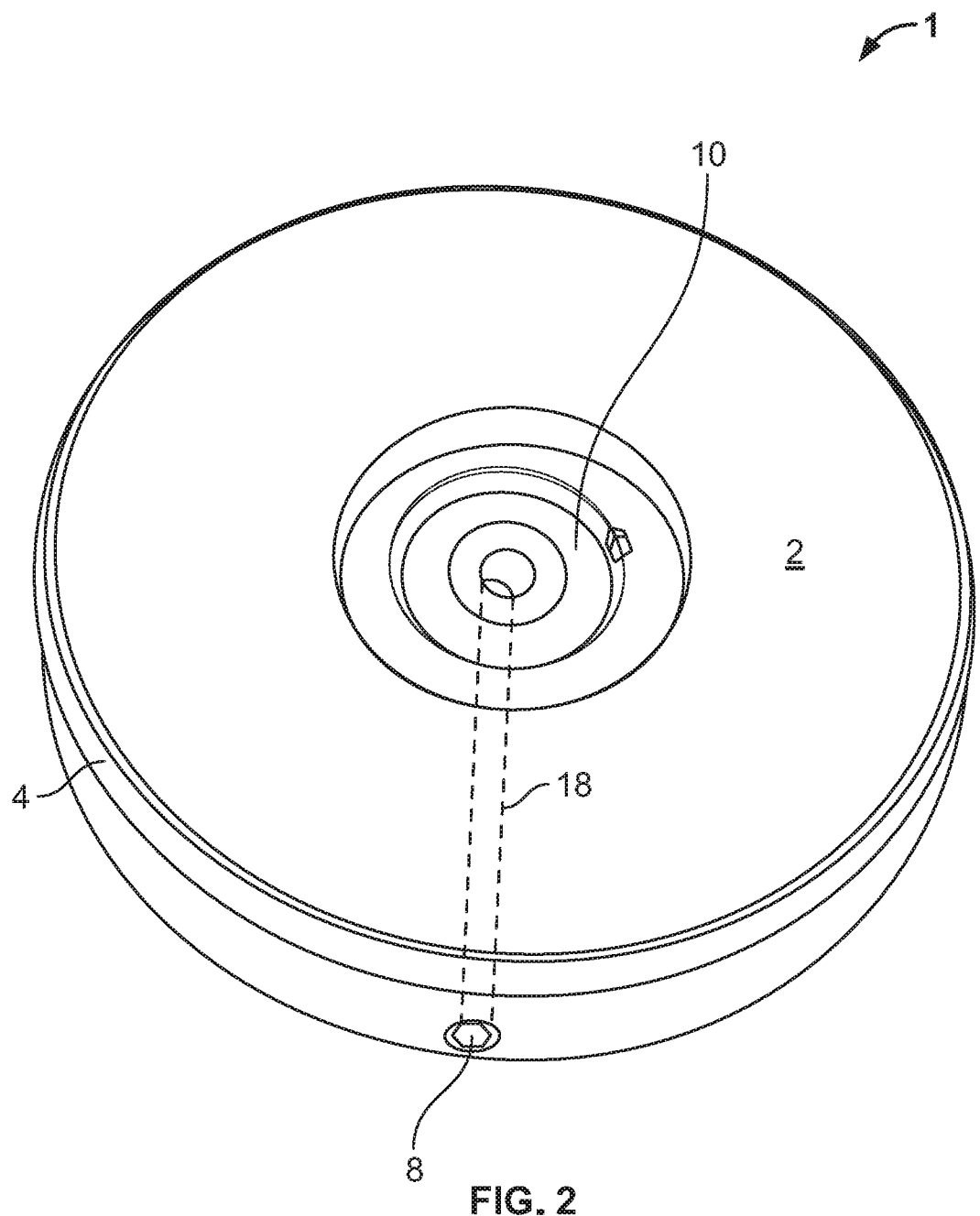
FIG. 2 illustrates an exemplary embodiment of the attachment plate with a removable filter.

Referring to FIGS. 1 and 2, an exemplary embodiment of the attachment plate for a prosthetic socket 1 is shown. The attachment plate 1 has a low-profile, rigid assembly that may be fabricated into the distal end of a prosthetic socket. In one exemplary embodiment, the attachment plate 1 includes a cylindrical body 2, a peripheral seal 4, a filter 6, an exhaust port 8, and a valve 10.

In some exemplary embodiments, the cylindrical body 2 may be made of plastic, metal, or other rigid material to facilitate a secure connection with the inner wall of a prosthetic socket. The valve 10 may be a one-way valve or a check valve that prevents air from flowing back into the cavity. The peripheral seal 4 may be an O-ring or a rubber or polymer layer around a side of the cylindrical body 2.

The exhaust port 8 allows air to be expelled from the cavity of the prosthetic socket. This is done by an air tunnel 18 running through the cylindrical body 2 from the exhaust port 8 to the valve 10. The valve 10 is open to the cavity to allow air to be removed from the cavity to create the vacuum to secure the prosthetic limb to a residual limb. The filter 6 may be removably affixed over the valve 10 to prevent debris from entering the valve 10 or the air tunnel 18.

In some exemplary embodiments, the exhaust port 8 may be configured to connect to mechanical or electrical pumps that draw air out of the cavity. In some embodiments that connect to an electric vacuum, there is no valve 10 in the cylindrical body 2, so the electric pump can read the level of vacuum in the cavity to maintain the desired level of vacuum.

While the attachment plate creates a seal at the distal end of the prosthetic socket, the proximal seal to close the system will be an industry standard suspension sleeve that seals on the skin of the user above a liner or a liner with a seal that will seal on the inside of the socket.

Figure 3:
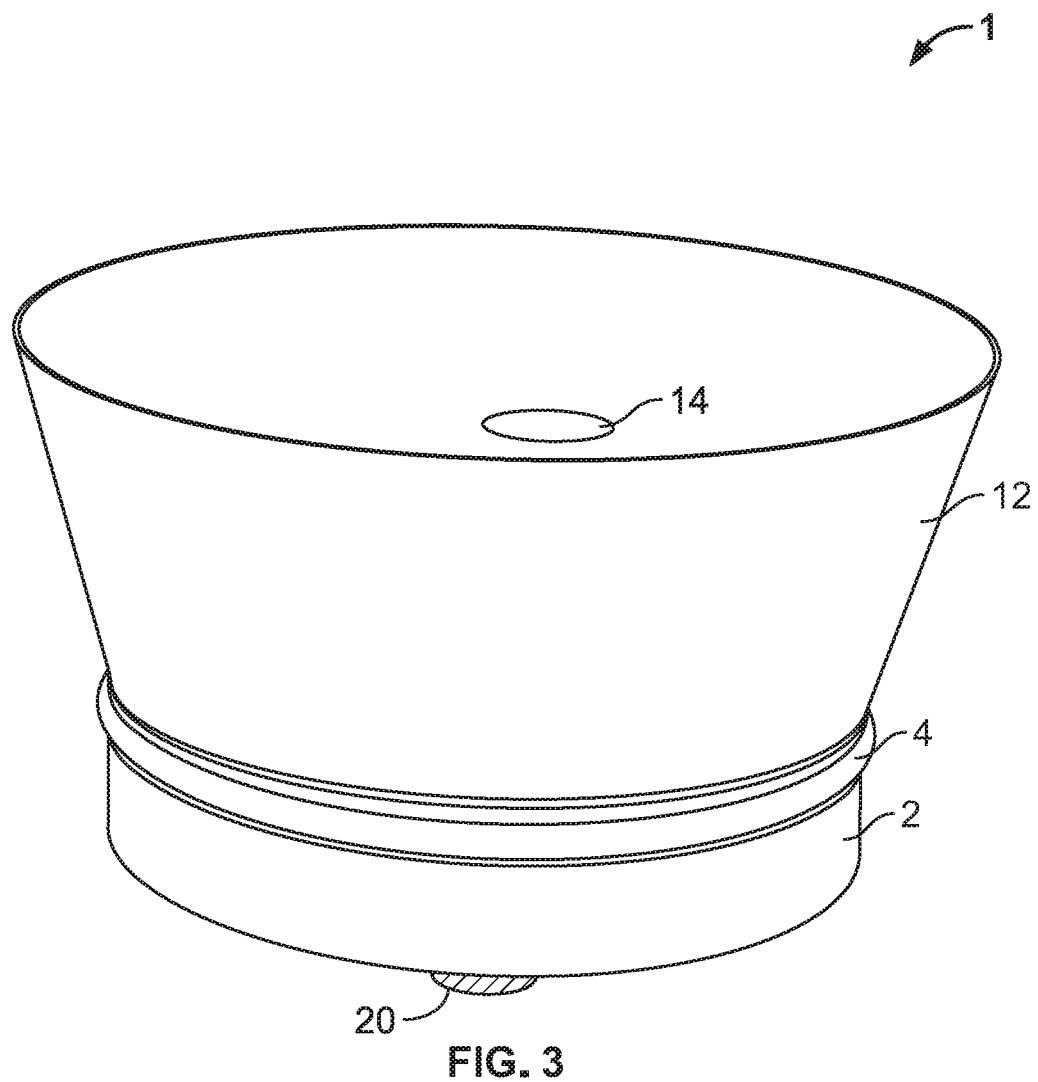
FIG. 3 illustrates another exemplary embodiment of the attachment plate with a distal end pad with hole for air expulsion.

Referring to FIG. 3, a distal end pad 12 is shown in use with the attachment plate 1. In some exemplary embodiments, the attachment plate 1 may be used with a distal end pad 12. The distal end pad 12 may be affixed to a top of the cylindrical body 2. In some embodiments, the distal end pad 12 has a channel 14 running through its center creating a channel from top to bottom. The channel 14 align over the valve 10 so that fluid communication with the cavity is maintained. In some embodiments, the distal end pad 12 has a concave top to receive a residual limb. In some embodiments, the distal end pad 12 may be custom molded to fit a specific residual limb. The distal end pad 12 may be made of a polymer, a thermoplastic elastomer, silicone, polyurethane, rubber, or other suitable material.

In embodiments with a distal end pad 12, the distal end pad 12 may be permanently affixed to the top of the cylindrical body 2 prior to molding the attachment plate 1 and distal end pad 12 into the distal end of the prosthetic socket.

Figure 4:
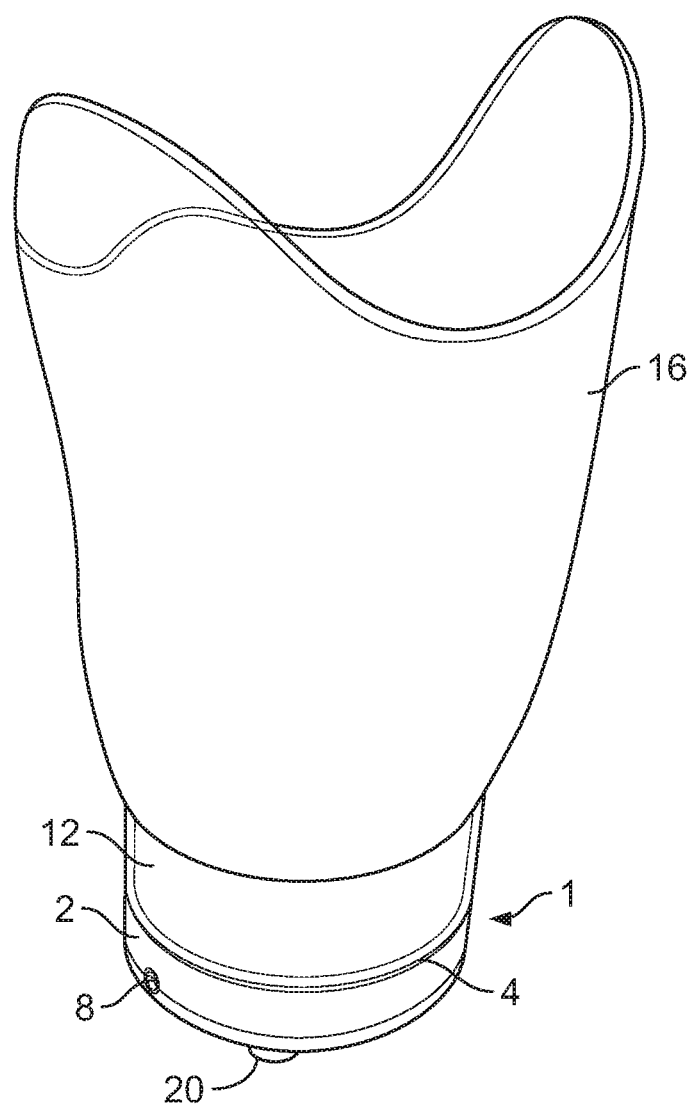
FIG. 4 illustrates the attachment plate and distal end pad are shown fabricated into a prosthetic socket.

Referring to FIG. 4, an exemplary prosthetic socket is shown with the attachment plate 1 and distal end pad 12 fabricated into the distal end of the prosthetic socket 16. By way of example, the attachment plate 1 and distal end pad 12 are fabricated into the prosthetic socket 16 by first creating a mold of the residual limb. The distal end pad 12 is affixed to the attachment plate 1. Then the distal end pad 12 is placed over the distal end of the residual limb mold. Layers of fiberglass or carbon and epoxy or thermoplastic sheets or any combination used by prosthetic technicians are then applied over tooling for the attachment plate 1, the distal end pad 12, and the mold of the residual limb. Once the socket is fabricated, the tooling is removed, and then the attachment plate 1 and distal end pad 12 are affixed into the cavity from the tooling. The peripheral seal 4 facilitates an air-tight seal between the attachment plate 1 and the inner wall of the prosthetic socket when the attachment plate 1 is fabricated into the distal end of the prosthetic socket. In one exemplary embodiment, the layers cover the peripheral seal 4 but leave the exhaust port 8 uncovered. This allows the attachment plate 1 to expel air to atmosphere instead of to an internal portion of the prosthetic socket.

By molding the distal end pad 12 and the attachment plate 1 into the prosthetic socket 16, the peripheral seal 4 directly contacts and presses against an inner wall of the prosthetic socket 16. This creates an air-tight seal between the attachment plate 1 and the prosthetic socket 16.

In some embodiments, a prosthetic socket 16 may be fabricated around tooling and the attachment plate 1 replaces the tooling. The tooling is a manufactured part having shape of the attachment plate 1 and distal end pad 12. The tooling includes posts that stick out of the distal end that clear the holes for the four-hole pattern of the mounting element 20, as well as leave a hole on the side of the socket for the exhaust port 8 to expel air.

In some exemplary embodiments, the attachment plate 1 includes a mounting element 20. The mounting element 20 is configured to affix to a prosthetic limb.

Figure 5:
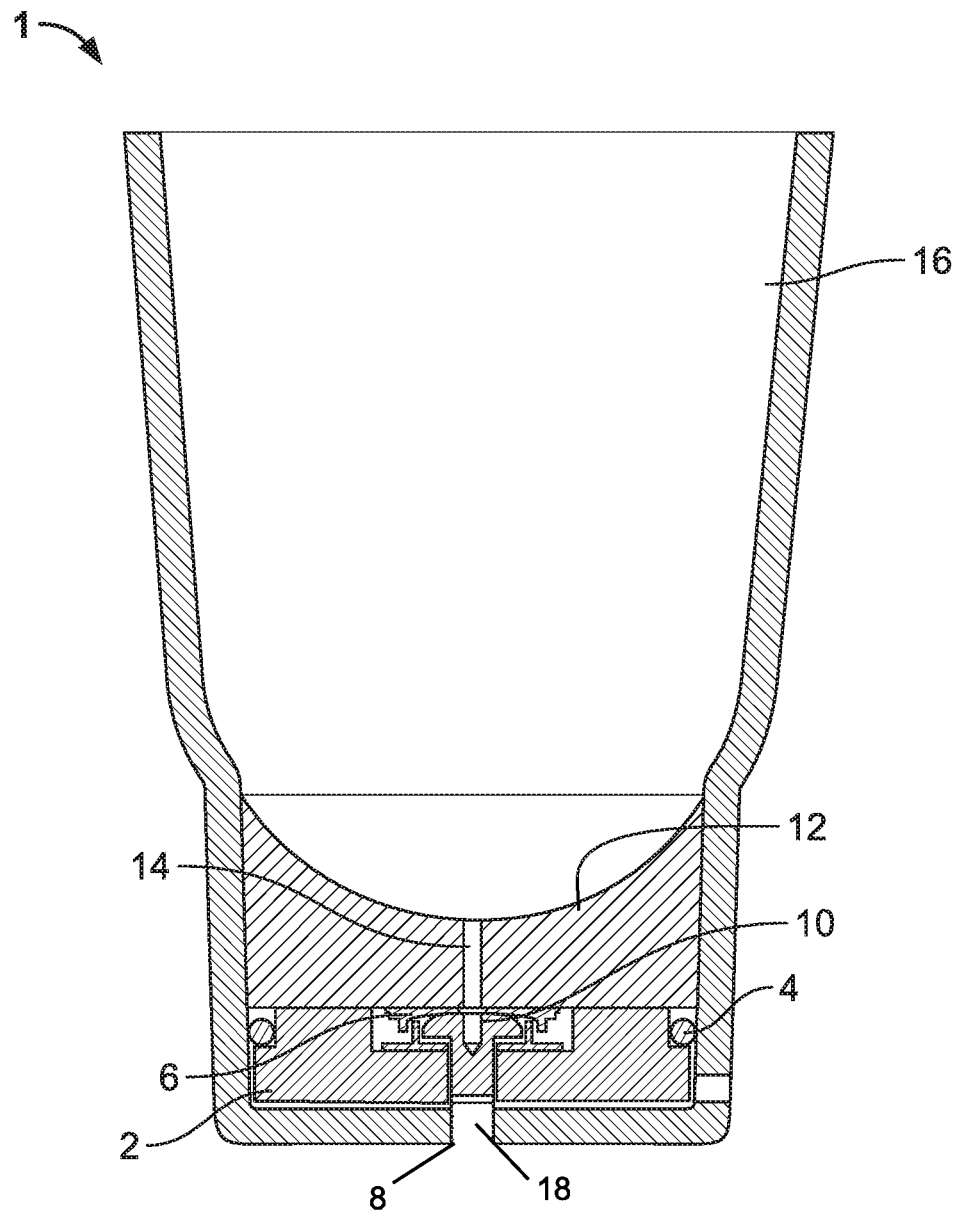
FIG. 5 is a cutaway view of one exemplary embodiment of the attachment plate and distal end pad shown attached to a prosthetic socket.

Referring to FIG. 5, a cutaway view of one exemplary embodiment of the attachment plate 1 with distal end pad 12 is shown fabricated into a socket 16. The cylindrical body 2 is located at the distal end of the prosthetic socket 16 with the peripheral seal 4 forming an air-tight seal against the inner wall of the prosthetic socket 16. The channel 14 through the distal end pad 12 is aligned above the filter 6 and intake valve 10 to expel air to the exhaust port 8 into the componentry and pylon of the prosthesis. In this exemplary embodiment, the exhaust port 8 is located on the bottom of the cylindrical body 2 beneath the valve 10.

In some exemplary embodiments, the attachment plate 1 includes a release mechanism 11. The release mechanism 11 is configured to allow air back into the cavity of the prosthetic socket 16 to release suction or vacuum. By way of example, the release mechanism 11 may be a push or pull button.

Figure 6:
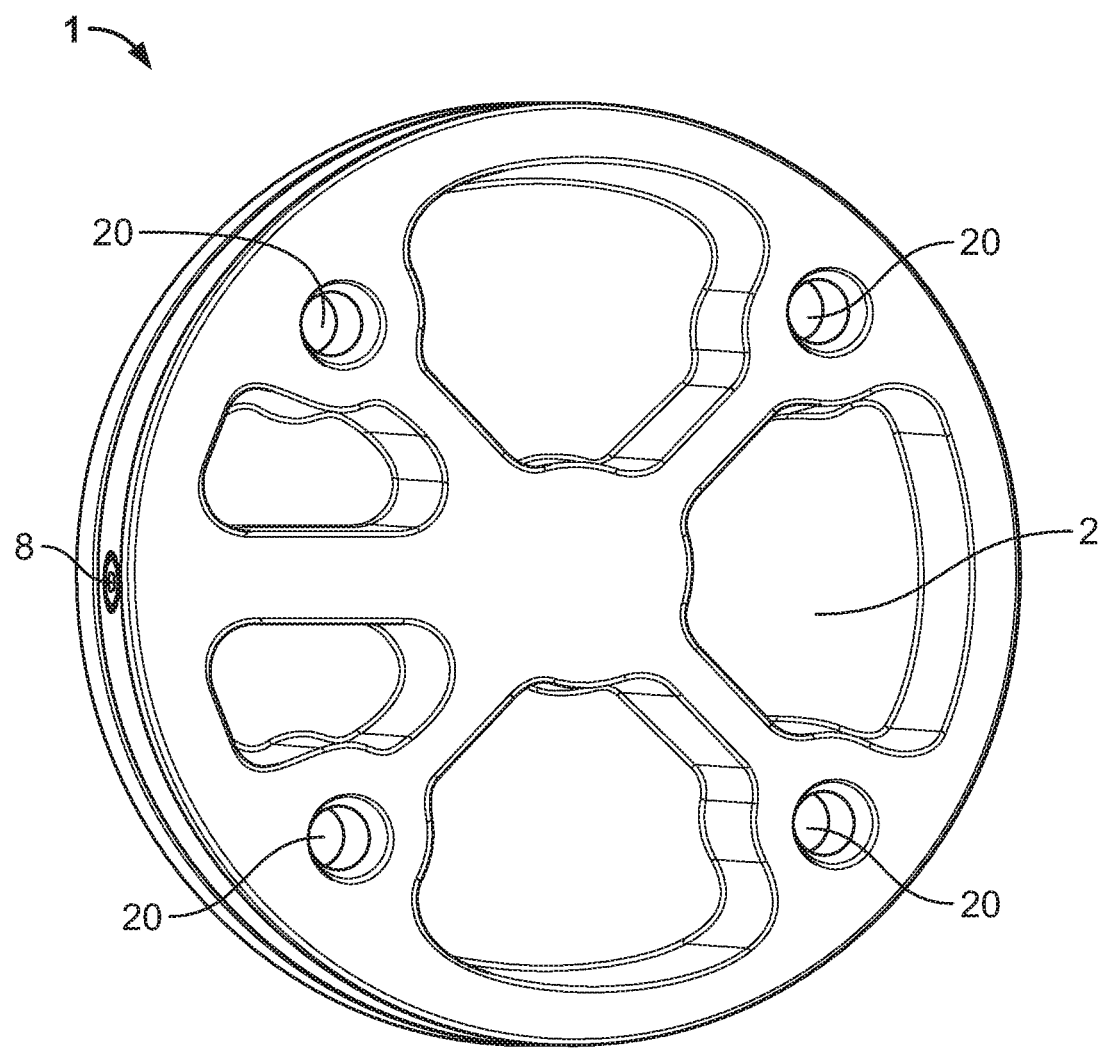
FIG. 6 is a bottom view of one exemplary embodiment of the attachment plate showing a mounting element with a four hole pattern.

Referring to FIG. 6, a bottom of one exemplary embodiment of the attachment plate 1 is shown. In this exemplary embodiment, the mounting element 20 is a 4-hole pattern that affixes a prosthetic limb to the socket. In this exemplary embodiment, instead of machining the attachment plate 1 plate entirely out of metal, it is possible to have a 4-hole pattern machined out of metal and over-mold plastic with the air passage detail in the plastic to reduce manufacturing steps and time of machining. It is also possible to mold the plate out of plastic, and heat stake threaded inserts to provide the 4-hole pattern.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the embodiments described herein are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. An attachment plate to be fabricated into a prosthetic socket, the attachment plate comprising:
    a cylindrical body, having a side, a top, and a bottom;
    a peripheral seal affixed to the side of the body;
    a valve located on the top of the cylindrical body;
    an exhaust port located on the side of the cylindrical body and in fluid communication with the valve, the exhaust port configured to expel air external to a cavity of the prosthetic socket;
    a distal end pad on the top of the body, the distal end pad having a flat bottom and a concave top; and
    a channel in the distal end pad fluidly connecting the cavity of the prosthetic socket to the valve.

2. The attachment plate of claim 1, further comprising an air tunnel through the body from the valve to the exhaust port.

3. The attachment plate of claim 1, wherein the prosthetic socket is fabricated around the cylindrical body.

4. The attachment plate of claim 1, wherein the cylindrical body in the distal end of the prosthetic socket and the peripheral seal secured against an inner surface of the prosthetic socket.

5. The attachment plate of claim 1, further comprising a mounting element located on the bottom of the cylindrical body.

6. An attachment plate fabricated into a distal end of a prosthetic socket, the attachment plate comprising:
    a cylindrical body having a top, a bottom, and a side;
    an exhaust port located on the side of the cylindrical body and configured to expel air out of the side of the cylindrical body;
    a peripheral seal affixed to the side of the cylindrical body and above the exhaust port, the peripheral seal contacting an inner surface of the distal end of the prosthetic socket to form an air-tight seal;
    a valve in the top of the cylindrical body, the valve in fluid communication with a cavity of the prosthetic socket;
    an air tunnel running through the cylindrical body and connecting the valve to the exhaust port;
    a distal end pad on the top of the body and extending into the cavity of the prosthetic socket, the distal end pad having a flat bottom and a concave top; and
    a channel in the distal end pad fluidly connecting the cavity of the prosthetic socket to the valve thereby allowing air to move from the cavity to the valve.

7. The attachment plate of claim 6, further comprising a removable filter affixed over the valve, the removable filter configured to prevent debris from the cavity to enter the valve or the air tunnel.

8. The attachment plate of claim 6, further comprising a mounting element on the bottom of the cylindrical body.

9. An attachment plate in a distal end of a prosthetic socket, the attachment plate comprising:
    a cylindrical body having a peripheral seal, the peripheral seal configured to create an air-tight seal when the attachment plate is configured to be fabricated into the distal end of the prosthetic socket;
    a valve on a top of the cylindrical body, the valve configured to allow air to flow out of a cavity of the prosthetic socket;
    an exhaust port located on a side of the cylindrical body and in fluid communication with the valve, the exhaust port configured to expel air to atmosphere;
    a mounting element, the mounting element configured to attach to a prosthetic limb; and
    a distal end pad on top of the body, the distal end pad having a flat bottom and a concave top; and
    a channel in the distal end pad fluidly connecting the cavity of the prosthetic socket to the valve thereby allowing air to move from the cavity to the valve.

10. The attachment plate of claim 9, further comprising an air tunnel, the air tunnel running through the cylindrical body from the valve to the exhaust port.

11. The attachment plate of claim 9, wherein the exhaust port is configured to attach to a vacuum pump.

12. The attachment plate of claim 9, further comprising a filter removably attached over the valve.

* * * * *